(12) United States Patent
Sabanayagam et al.

(10) Patent No.: US 6,284,497 B1
(45) Date of Patent: Sep. 4, 2001

(54) NUCLEIC ACID ARRAYS AND METHODS OF SYNTHESIS

(75) Inventors: Chandran R. Sabanayagam, Allston; Takeshi Sano, Needham, both of MA (US); John Misasi, Syracuse, NY (US); Anson Hatch, Seattle, WA (US); Charles Cantor, Del Mar, CA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/287,781

(22) Filed: Apr. 8, 1999

Related U.S. Application Data

(60) Provisional application No. 60/081,254, filed on Apr. 9, 1998.

(51) Int. Cl.[7] .............................. C12P 19/34; C12Q 1/68; G01N 33/00; C07H 21/02; C07H 21/04
(52) U.S. Cl. .......................... 435/91.2; 435/6; 435/91.1; 436/94; 536/23.1; 536/24.3; 536/24.33
(58) Field of Search ........................... 435/6, 91.1, 91.2, 435/183; 536/23.1, 24.3, 24.33, 25.3; 436/501, 94

(56) References Cited

U.S. PATENT DOCUMENTS

| | | |
|---|---|---|
| 5,143,854 | 9/1992 | Pirrung et al. . |
| 5,714,320 | 2/1998 | Kool . |
| 5,770,722 | 6/1998 | Lockhart et al. . |
| 5,854,033 * | 12/1998 | Lizardi ........................... 435/6 |
| 5,874,219 | 2/1999 | Rava et al. . |
| 6,054,274 * | 4/2000 | Sampson et al. ............... 435/6 |
| 6,143,495 * | 11/2000 | Lizardi et al. .................. 435/6 |

OTHER PUBLICATIONS

Baner et al., *Nucleic Acid Res.* 26: 5073–8 (1998).
Schepinov et al., *Nucl. Acid Res.* 25: 1155–61 (1997).
Fire and Xu, *Proc. Natl. Acad. Sci. USA* 92: 4641–5 (1995).
Kwoh et al. *Proc. Natl. Acad. Sci. USA* 86: 1173 (1989).
Mullis et al. *CSH Symp. Quant. Biol.* 51: 263–73 1986).

* cited by examiner

*Primary Examiner*—Ethan Whisenant
*Assistant Examiner*—Frank Lu
(74) *Attorney, Agent, or Firm*—Nixon Peabody LLP

(57) ABSTRACT

The present invention generally relates to high density nucleic acid arrays and methods of synthesizing nucleic acid sequences on a solid surface. Specifically, the present invention contemplates the use of stabilized nucleic acid primer sequences immobilized on solid surfaces, and circular nucleic acid sequence templates combined with the use of isothermal rolling circle amplification to thereby increase nucleic acid sequence concentrations in a sample or on an array of nucleic acid sequences.

22 Claims, 9 Drawing Sheets

NUCLEIC ACID ARRAYS AND METHODS OF SYNTHESIS

PRIOR APPLICATIONS

The present application claims priority from U.S. Provisional Patent Application Ser. No. 60/081,254, filed Apr. 9, 1998. This prior application is incorporated herein by reference.

GOVERNMENT RIGHTS

The development of the present invention was supported under Contract Number DE-FG02-93ER61609 awarded by the Department of Energy and Contract No. DAAH04-95-1-0358 awarded by the Army Research Office. The United States Government may have certain rights in this invention.

FIELD OF THE INVENTION

The present invention generally relates to high density nucleic acid arrays and methods of synthesizing oligonucleotides on a solid surface. Specifically, the present invention contemplates the use of stabilized nucleic acid primer sequences immobilized on solid surfaces, and circular nucleic acid sequence templates combined with the use of isothermal rolling circle amplification to thereby increase oligonucleotide concentrations in a sample or on an array of oligonucleotides.

BACKGROUND OF THE INVENTION

It is estimated that the human genome encodes from 60,000 to 100,000 different genes, and that certain mutations in the genome lead to dysfunctional proteins, giving rise to a multitude of diseases. Assays capable of detecting the presence of particular mutations in a DNA sample are of substantial importance in forensics, medicine, epidemiology, public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples.

Technologies are presently available that automate the processing and interpretation of such assays. For example, U.S. Pat. No. 5,874,219 to Rava, et al., teaches processing multiple chip assays by providing biological chips comprising molecular probe arrays. The biological chip is subjected to manipulation by fluid handling devices that automatically perform steps to carry out reactions between target molecules in the samples and probes. The chip is further subjecting to a reader that examines the probe arrays to detect any reactions between target molecules and probes. While this sophisticated technology is useful, the sensitivity of detection assays generally is often limited by the concentration at which a particular target nucleic acid molecule is present in a sample. Thus, methods that are capable of amplifying the concentration of nucleic acid molecules must be developed as important adjuncts to detection assays.

Methods of synthesizing desired single stranded DNA sequences are well known to those of skill in the art. In particular, methods of synthesizing oligonucleotides are found in, for example, *Oligonucleotide Synthesis: A Practical Approach,* Gait, ed., IRL Press, Oxford (1984). Methods of forming large arrays of oligonucleotides, peptides and other polymer sequences have been devised. Of particular note, Pirrung et al., U.S. Pat. No. 5,143,854, incorporated herein by reference, disclose methods of forming arrays of peptides, oligonucleotides and other polymer sequences using, for example, light-directed synthesis techniques. However, the above techniques produces only a relatively low concentrations of DNA; that is, the number of DNA on the array is limited to surface area.

One approach for overcoming the limitation of DNA concentration is to selectively amplify the nucleic acid molecule whose detection is desired prior to performing the assay. Recombinant DNA methodologies capable of amplifying purified nucleic acid fragments in vivo have long been recognized. Typically, such methodologies involve the introduction of the nucleic acid fragment into a DNA or RNA vector, the clonal amplification of the vector, and the recovery of the amplified nucleic acid fragment. An example of such methodologies are provided by, for example, *Molecular Cloning, A Laboratory, Manual,* 2nd Ed., ed. by Sambrook, Fritsch and Maniatis (Cold Spring Harbor Laboratory Press, 1989), incorporated herein by reference. However, these methods are limited because the concentration of a target molecule in a sample under evaluation is so low that it cannot be readily cloned.

In an effort to solve such limitations, other methods of in vitro nucleic acid amplification have been developed that employ template directed extension. In such methods, the nucleic acid molecule is used as a template for extension of a nucleic acid primer in a reaction catalyzed by polymerase. One such template extension method is the "polymerase chain reaction" ("PCR"); see Mullis, K. et al., Cold Spring Harbor, *Symp. Quant. Biol.,* 51:263–273 (1986), incorporated herein by reference. PCR technology has several deficiencies. First, it requires the preparation of two different primers which hybridize to two oligonucleotide sequences of the target sequence flanking the region that is to be amplified. The concentration of the two primers can be rate limiting for the reaction. A disparity between the concentrations of the two primers can greatly reduce the overall yield of the reaction. The reaction conditions chosen must be such that both primers "prime" with similar efficiency. Since the two primers necessarily have different sequences, this requirement can constrain the choice of primers and require considerable experimentation. Finally, PCR requires the thermocycling of the molecules being amplified. The thermocycling requirement attenuates the overall rate of amplification because further extension of a primer ceases when the sample is heated to denature double-stranded nucleic acid molecules. Thus, to the extent that the extension of any primer molecule has not been completed prior to the next heating step of the cycle, the rate of amplification is impaired.

Other known nucleic acid amplification procedures include transcription-based amplification systems; for example, see Kwoh D. et al., *Proc. Natl. Acad. Sci. (U.S.A.),* 86:1173 (1989). These methods are limited in that the amplification procedures depend on the time spent for all molecules to have finished a step in a cycling method. Particular molecules used to perform the method have different enzymatic rates. Molecules with slower enzymatic rates would slow down molecules with faster enzymatic rates in the cycle. This slowing down of the faster acting enzymes leads to a lower exponent of amplification, and hence, a lower concentration of DNA. Examples of others systems developed to amplify nucleotide sequences are described in U.S. Pat. No. 5,854,033 to Lizardi, incorporated herein by reference. Lizardi, however, does not describe solid surface immobilization of the primers used for extension, as the Lizardi method is performed in solution. This reference is therefore limited because it does not allow for the immobilization of the oligonucleotides, does not form an array, and hence suffers from the same deficiencies as the other methods described above.

Clearly, there is a great need for DNA arrays that allow for higher concentrations of DNA. Furthermore, approaches are needed to synthesize the arrays and particular target nucleic acid molecules at increased concentrations.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, for purposes of the present invention, the following terms are defined below.

The term "rolling circle amplification" ("RCA") as used herein describes a method of DNA replication and amplification that results in a strand of nucleic acid comprising one or more copies of a sequence that is a complimentary to a sequence of the original circular DNA. This process for amplifying (generating complimentary copies) comprises hybridizing an oligonucleotide primer to the circular target DNA, followed by isothermal cycling (e.g., in the presence of a ligase and a DNA polymerase). A single round of amplification using RCA results in a large amplification of the sequences in the circular target to obtain a high concentration the desired oligonucleotide on a single strand of nucleic acid. Because the desired nucleic acid sequence becomes the predominant sequence (in terms of concentration) in the mixture, it is said to be "RCA amplified". With RCA, it is possible to amplify a single copy of a particular nucleic acid sequence to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In particular, the resulting nucleic acid comprising amplified nucleic acid sequences created by the RCA process are, themselves, efficient templates for subsequent RCA amplifications. Solid Surface Rolling Circle Amplification ("ssRCA") refers to RCA that occurs when the oligonucleotide which hybridizes to the circular DNA is attached to a solid surface. The term "RCA product" as used herein refers to the resultant nucleic acid comprising at least three (and preferably many more) copies of the desired sequence contained within the circular DNA.

The term "high density" as used herein refers to the high number of nucleic acid repeated sequences that may be obtained by the methods of the present invention. The term "nucleic acid repeated sequences" as used herein refers to the sequential repeating of a given nucleic acid sequence that is achieved by the amplification of the rolling circle amplification arrays or methods of the present invention. For example, the concentration of a target species in a sample under evaluation is increased do to the amplification of the template directed repeating extension. High density in the present application is not dependant on the surface density of the oligonucleotides; rather, density is volume dependant ("volume density"). The definition of density in the present invention therefore defines the volume density of oligonucleotides in terms of the "Z" plane, or three-dimensional space, as opposed to the prior art attempts to define density in the "X/Y", or two-dimensional plane. Because density is not limited by the physical constraints of the two-dimensional surface, the potential number of oligonucleotides on the array is much greater. The terms "ordered redundant array" and "ordered array" as used herein, refer to the orientation of nucleic acid sequences on the Z plane, or three-dimensional space, or in the in the X/Y, or two-dimensional plane, respectively.

An ordered redundant array is "redundant" in the sense that sequences of interest (e.g., used for hybridization) are repeated in the array. Rather than achieving this redundancy by adding repeated sequences to the X/Y plane of the solid support, the present invention contemplates achieving redundancy by introducing repeating sequences in the growing strand (in the Z dimension) as the primer is extended using the circular template.

The term "nucleic acid repeat sequence" as used herein, can be used interchangeably, and has the same meaning, as the term "concatamer". A DNA concatamer consists of two or more DNA fragments which have been joined to produce a single DNA chain. This product can be single-stranded or double-stranded DNA. Usually, concatamers consist of a specific nucleotide sequence which is repeated. Concatamers usually consist of several to hundreds of repeats. A "dimer" is defined as two repeats. A "trimer" is defined as three repeats. A "tetramer" is defined as four repeats. Concatamers are usually more than several repeats. For example, if the monomeric nucleotide sequence is: (N1-N2-N3- . . . -Nn), where N1 through Nn define a specific nucleotide sequence, then (N1-N2-N3- . . . Nn)m is a concatamer if that sequence contains m repeats. The total length of the concatamer is thus n×m. The volume density of the present invention can be calculated by multiplying the number of concatamers in a given oligonucleotide by the number of oligonucleotides attached to the solid surface. The only limitations on the volume density are the respective half life of the polymerases, or the amount of precursor deoxyribonucleotides or ribonucleotides that are added during the polymerase reaction.

The term "hybridization" as used herein involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA,* 46:453 (1960) and Doty et al., *Proc. Natl. Acad. Sci. USA,* 46:461 (1960) have been followed by the refinement of this process into an essential tool of modern biology. The term "secondary hybridization" as used herein refers to the annealing of probe or tagging molecules to the extended "nucleic acid repeated sequences" or "concatamers" of the present invention.

The term "complementary" or "substantially complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See M. Kanehisa, *Nucleic Acids Res.,* 12:203 (1984), incorporated herein by reference. The term "at least a portion of" as used herein, refers to the complimentarity between a circular DNA template and an oligonucleotide primer of at least one base pair.

Partially complementary sequences will hybridize under low stringency conditions. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

The term "nucleic acid sequence" as used herein is defined as a molecule comprised of two or more deoxyribonucleotides or ribonucleotides. The exact length of the sequence will depend on many factors, which in turn depends on the ultimate function or use of the sequence. The sequence may be generated in any manner, including chemical synthesis, DNA replication, reverse transcription, or a combination thereof. Due to the amplifying nature of the present invention, the number of deoxyribonucleotides or ribonucleotides bases within a nucleic acid sequence may be virtually unlimited. The term "oligonucleotide," as used herein, is interchangeably synonymous with the term "nucleic acid sequence".

The term "primer" as used herein refers to a sequence of nucleic acid attached to a solid surface, and used for rolling circle amplification. The primer may be complimentary or substantially complimentary to a portion of the circular template.

The term "Solid Surface" as used herein refers to a material having a rigid or semi-rigid surface. Such materials will preferably take the form of chips, plates, slides, small beads, pellets, disks or other convenient forms, although other forms may be used. In some embodiments, at least one surface of the solid surface will be substantially flat. In other embodiments, a roughly spherical shape is preferred.

The term "nucleic acid sequence of interest" refers to any nucleic acid sequence the manipulation of which may be deemed desirable for any reason by one of ordinary skill in the art (e.g., for nucleic acid sequence amplification or detection purposes). The term "sequence of interest being different" refers to a comparison of the base sequence of at least two nucleic acid molecules. The differences may be single base differences or may involve many bases.

SUMMARY OF THE INVENTION

Arrays of oligonucleotides have previously been proposed for sequencing target nucleic acid by hybridization. In the prior methods, groups of contiguous bases are determined simultaneously by hybridization, rather than by sequencing one base at a time using conventional Sanger sequencing. The approach utilizes oligonucleotides (of length n) immobilized on a solid support in large numbers in an ordered array. The array is designed such that the sequences of all of the oligonucleotides (collectively) represents the complete sequence of the target. Thus the target can be fractionated into smaller pieces which can hybridize to the oligonucleotides on the array.

One important drawback to current approaches for such arrays is the inconvenience of chemically synthesizing each distinct oligonucleotide necessary to represent (collectively) the entire target sequence, particularly if such oligos are long (e.g., greater than twenty nucleotides). Moreover, since space on the solid support is limited—and yet large numbers of such oligonucleotides are needed—there is little room for redundancy, i.e., an array containing two identical nucleotide sequences.

The present invention contemplates solving both problems by utilizing circular nucleic acid in the production of the array. The method contemplates a solid support with positions for oligonucleotides defined by x and y coordinates. At each position (e.g., x1, y1; x1, y2; etc.), a oligonucleotide is immobilized. In one embodiment (see FIG. 1A), the same oligonucleotide (i.e., an oligonucleotide with the same generic nucleotide sequence (SEQ ID NO: 1)) is immobilized in every position (or nearly every position, with some positions left empty or for controls) on the solid support. In this embodiment, a circular DNA template comprising i) a region having a sequence complementary to at least a portion of said generic oligonucleotide (shown in FIG. 1A as AAAACC; SEQ ID NO: 2), and ii) a region comprising a sequence of interest (shown in FIG. 1A as QQQQetc.) is employed. The region having a sequence complementary to at least a portion of said generic oligonucleotide permits hybridization of the circular template to the immobilized oligonucleotide (FIG. 1A is merely illustrative and is not meant to limit the sequence or length of the sequence of this hybridizing region; indeed, regions larger than six nucleotides are preferred). The sequence of interest may comprise a portion of the sequence of a target of interest (e.g., cancer gene, histocompatibility gene, etc.). To create an array with diverse sequences, a circular DNA template is added at each position (e.g., by a robot), wherein each circular DNA template added has a unique sequence of interest (e.g., a different sequence corresponding to a unique portion of a target). Each circular DNA template is added under conditions such that the circular DNA template hybridizes with the generic immobilized oligonucleotide (SEQ ID NO: 1), said immobilized oligonucleotide thereafter being extended by a polymerase to create a unique extended nucleic acid strand at each position on the solid support, such extended strands comprising two or more (and more typically three or more, and more preferably, ten or more, and still more preferably more than fifty) copies of the sequence of interest. Thereby, an array is created with redundancy in the z dimension (i.e., out of the x and y plane of the solid support). Variations on this first embodiment, include (but are not limited to) circular templates with more than one copy of the sequence of interest (see the larger circular template in FIG. 1A which includes, in a circular DNA molecule, which is merely illustrative and not intended to limit such templates to comprising only two copies, i.e., greater than two copies is also contemplated). Of course, such larger templates still need a region that will hybridize to the generic immobilized oligonucleotide (SEQ ID NO: 1). Such larger templates may (or may not) contain other regions such as regions that separate each copy of the sequence of interest (such a separating region is depicted in FIG. 1A as WWWW, the number of nucleotides "W" being variable between 0 and 100). The invention contemplates that such regions that separate each copy of the sequence of interest can be additional regions that can hybridize to the generic immobilized oligonucleotide (e.g., the WWWW of FIG. 1A could be replaced with yet another region defined by AAAACC; SEQ ID NO: 2).

FIG. 1B shows an alternative embodiment, wherein a generic immobilized oligonucleotide is not employed. In this case, each immobilized oligonucleotide comprises a region comprising a different sequence (FIG. 1B is merely illustrative, showing one such oligonucleotide with one such unique sequence; SEQ ID NO: 1), each different sequence being complementary to a sequence of interest on a circular template. The circular DNA template comprises i) a first region comprising a sequence of interest (shown in FIG. 1B as ACGATAAAACC; SEQ ID NO: 3) and ii) a second region (shown in FIG. 1B as QQQQetc.) is employed. Because each immobilized oligonucleotide is unique, the region having a sequence complementary to at least a portion of the circular template permits hybridization only to the "corresponding" circular template; thus, the region permitting hybridization on the circular template is also the sequence of interest (FIG. 1B is merely illustrative and is not meant to limit the sequence or length of the sequence of this hybridizing region; indeed, regions larger than thirteen nucleotides are preferred). Each circular DNA template is added under conditions such that the circular DNA template hybridizes and thereafter the oligonucleotide is extended by a polymerase to create a unique extended nucleic acid strand at each position on the solid support, such extended strands comprising two or more (and more typically three or more, and more preferably, ten or more, and still more preferably more than fifty) copies of the sequence of interest. Thereby, an array is created with redundancy in the z dimension (i.e., out of the x and y plane of the solid support). Variations on this first embodiment, include (but are not limited to) circular templates with more than one copy of the sequence of interest (see the larger circular template in FIG. 1B, which includes, in a circular DNA molecule, which is merely illustrative and not meant to limit the invention on only a certain number of copies). Such larger templates may (or may not) contain other regions such as regions that separate each copy of the sequence of interest (such a separating region is depicted in FIG. 1B as WWWW, the number of nucleotides "W" being variable between 0 and 100). The number of such other regions not being limited to the number of copies (although it may be convenient to insert one such region between each copy of the sequence of interest).

The present invention makes available novel nucleic acid arrays, and novel methods to synthesize nucleic acid sequences on solid surfaces using nucleic acid primer sequences, circular nucleic acid template sequences, and isothermal rolling-circle amplification, as well as methods of using the arrays and methods for the detection of nucleic acid sequences.

The present invention contemplates an array of nucleic acid sequences, comprising a solid support having at least one surface; and a plurality of nucleic acid sequences attached to said surface of said solid support, wherein each said nucleic acid sequence is attached to said surface on different physical areas of said surface, and each nucleic acid sequence may contain sequentially identical or different deoxyribonucleotide or ribonucleotide bases. It is not intended that the present invention be limited to identical nucleic acid sequence within the arrays. A variety of arrays are contemplated. For example, the nucleic acid sequences of the present invention may be sequentially identical or different within the array. The present invention also contemplates varying sizes of the circular template.

Another embodiment of the present invention is to provide nucleic acid arrays that are produced by a process comprising the steps of providing circular single-stranded nucleic acid templates having a sequence, and immobilized linear partially single-stranded nucleic acid oligonucleotide primers having a sequence complementary to at least a portion of said sequence of said circular single-stranded nucleic acid templates, and mixing said circular single-stranded nucleic acid templates with said partially single-stranded nucleic acid oligonucleotide primers to create a mixture under conditions such that at least a portion of said circular single-stranded nucleic acid templates hybridize to said partially single-stranded oligonucleotide primers, and treating said mixture under conditions such that said immobilized linear partially single-stranded nucleic acid primers are extended. It is not intended that the present invention be limited to the exact conditions in the above process to produce the nucleic acid arrays. A variety of conditions are contemplated. For example, the arrays of the present invention may be produced with simple condition modifications known to those skilled in the art (e.g., varying nucleic acid sequences, polymerase types, ligase types, or surface types). Furthermore, It is not intended that the present invention be limited to the exact sequence of method steps described in the above process to produce the nucleic acid arrays. Other steps are contemplated. For example, upon primer sequence attachment to a solid surface, a second primer sequence may be hybridized to the first primer, followed by the addition of circular or semi-circular template sequences to be hybridized to the second primer sequence. RCA can then be carried out as in the first description above, and the resulting concatamer visualized via a florescent tagging or other detection method. The resulting array is therefore contemplated as a product of this series of steps.

Another embodiment of the present invention is to provide a method of determining the amount of specific template nucleic acid sequences present in a sample where the signal level measured is proportional to the amount of a template sequence in a sample and where the ratio of signal levels measured for different template sequences substantially matches the ratio of the amount of the different template sequences present in the sample.

Another embodiment of the present invention is to provide a method of detecting and determining the amount of multiple specific template nucleic acid sequences in a single sample where the ratio of signal levels measured for different template nucleic acid sequences substantially matches the ratio of the amount of the different template nucleic acid sequences present in the sample.

Another embodiment of the present invention is to provide a method of detecting the presence of template nucleic acid sequences representing individual alleles of a template genetic element.

Another embodiment of the present invention contemplates the use of molecular stabilizer nucleic acid sequences (e.g., stabilized with a second primer thereby forming a partially double-stranded and partially single-stranded primer) to reduce stearic hindrance of a nucleic acid primer sequence and thereby increase fidelity of the isothermal rolling circle amplification of DNA sequences. The present invention is not intended to be limited by any specific stabilizer length or configuration. A variety of lengths and configurations are contemplated. For example, a stabilizer nucleic acid sequence may be long or short, single or double stranded, or be comprised of any type of nucleic acid, including polypeptide nucleic acid (PNA).

Another embodiment of the present invention contemplates an allele-specific nucleic acid template sequence circularization, mediated by DNA ligase. A DNA template is considered circularized or "closed" when perfect hybridization between the template sequence and the nucleic acid primer sequence allows ligase to covalently circularize the template. Mismatches around the ligation site prevent template circularization, resulting in a non-circularized or "open" template. DNA polymerase is then used to preferentially amplify the closed templates, via ssRCA. The present invention is not intended to be limited by any specific ligation site hybridization. A variety of ligation site hybridizations are contemplated. For example, hybridization can be achieved by any base pairs that will bind to their complimentary base, regardless of the sequence order.

Another embodiment of the present invention contemplates the detection of single-nucleotide polymorphisms (SNP). Successful SNP detection can be performed by three coupled steps: hybridization of the primer nucleic acid sequence to nucleic acid template sequence, proofreading by DNA ligase, and replication of the template sequence (see FIG. 2). The invention contemplates a nucleic acid template sequence, P1 (SEQ ID NO: 4), that was designed to circularize via hybridization on two immobilized nucleic acid primer sequences, T1 (SEQ ID NO: 5) and T2 (SEQ ID NO: 6). T1 (SEQ ID NO: 9) and T2 (SEQ ID NO: 10) differ by only a single nucleotide such that the P1/T1 complex forms 30 contiguous base pairs, while the P1/T2 complex contains a C:T mismatch at the 5'-terminus of P1. This sequence recognition step is similar to hybridization on arrays, and it is difficult to distinguish between the P1/T1 and P1/T2 complexes because, in general, 3'- and 5'-end mismatches do not greatly affect duplex stability. The proofreading step is mediated by DNA ligase, because this enzyme is sensitive to single-base mismatches. When hybridized around the ligation point, the 3'-hydroxyl and 5'-phosphate of P1 can be successfully joined to form a covalently-closed circular template. Thus, DNA ligase can be used as a proofreading enzyme to change the topological structure of the template in a (+) or (−) type reaction. The (+) being the "closed" nucleic acid template sequence, and the (−) constituting the "open" nucleic acid template sequence. The ssRCA is achieved by DNA polymerase in an extension reaction primed by the 3'-hydroxyl of the primer sequences. In the case of circularized (closed) templates, extension occurs via ssRCA. In contrast, only partial extension is possible with non-circularized (open) templates. Using isotopically labeled nucleotides during the extension reaction, a $10^2$–$10^3$ fold more nucleotide incorporation with P1/T1than with 5'- or 3'-mismatched template/primer complexes was observed. However, the present invention is not limited to the specific sequence of steps described above. Different ordering of the steps in the method are also contemplated. For example, upon primer sequence attachment to a solid surface, a second primer sequence may be hybridized to the first primer, followed by the addition of circular or semi-circular template sequences to be hybridized to the second primer sequence. RCA can then be carried out as in the first description above, and the resulting concatamer visualized via a florescent tagging or other detection method.

BRIEF DESCRIPTION OF THE DRAWINGS

FIG. 3B illustrates that as RCA continues around the circular template sequence, the RCA product is displaced and rolls providing essentially unlimited concatamer length.

FIG. 3C shows the results of DNA polymerase on an uncircularized (non-ligated) template sequence. As can bee seen, only a partial primer extension is achieved in this instance. The difference in ligated versus non-ligated sequences is monitored using $^{32}$P-labeled nucleotides which are incorporated into the polymerizing DNA. Thus a ligated template is observed as having more radioactivity after DNA polymerization compared to an unligated template.

FIG. 5 is an autoradiogram of the chip reaction using (A) Φ29 DNA polymerase or (B) *E. coli* DNA polymerase. The left columns in the autoradiograms are wells containing primer sequences which hybridize perfectly to the template sequences; the right column contain primers which create a 5'-end mismatch with the templates. Although both polymerases yielded approximately 3-fold differences between the matched and mismatched targets, Φ29 DNA polymerase generated more, or longer concatamers than *E. coli* polymerase.

DESCRIPTION OF THE INVENTION

Figure 1A:
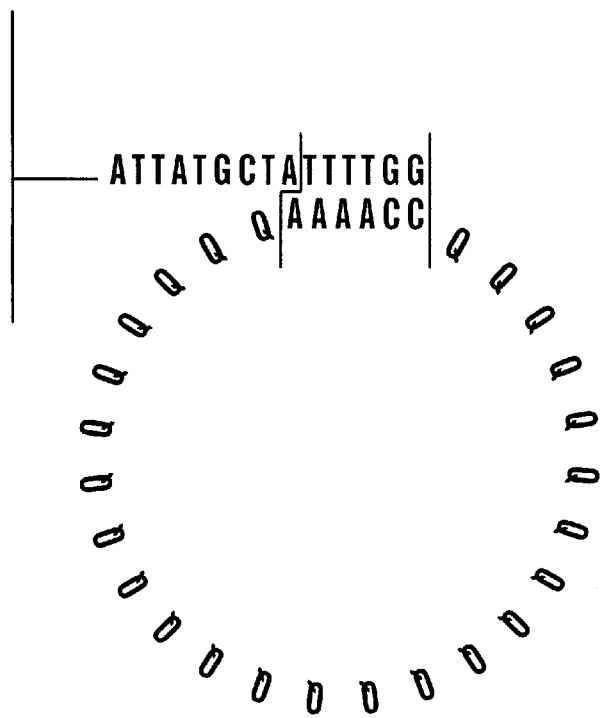
FIGS. 1A and 1B are schematic representations of oligonucleotide primers and oligonucleotide templates. For much greater description of these Figures, see the summary of the invention section, supra.
Figure 1A:
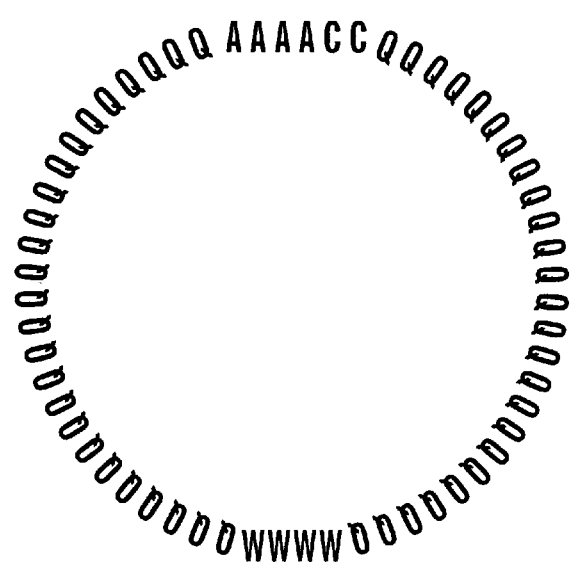
Figure 1B:
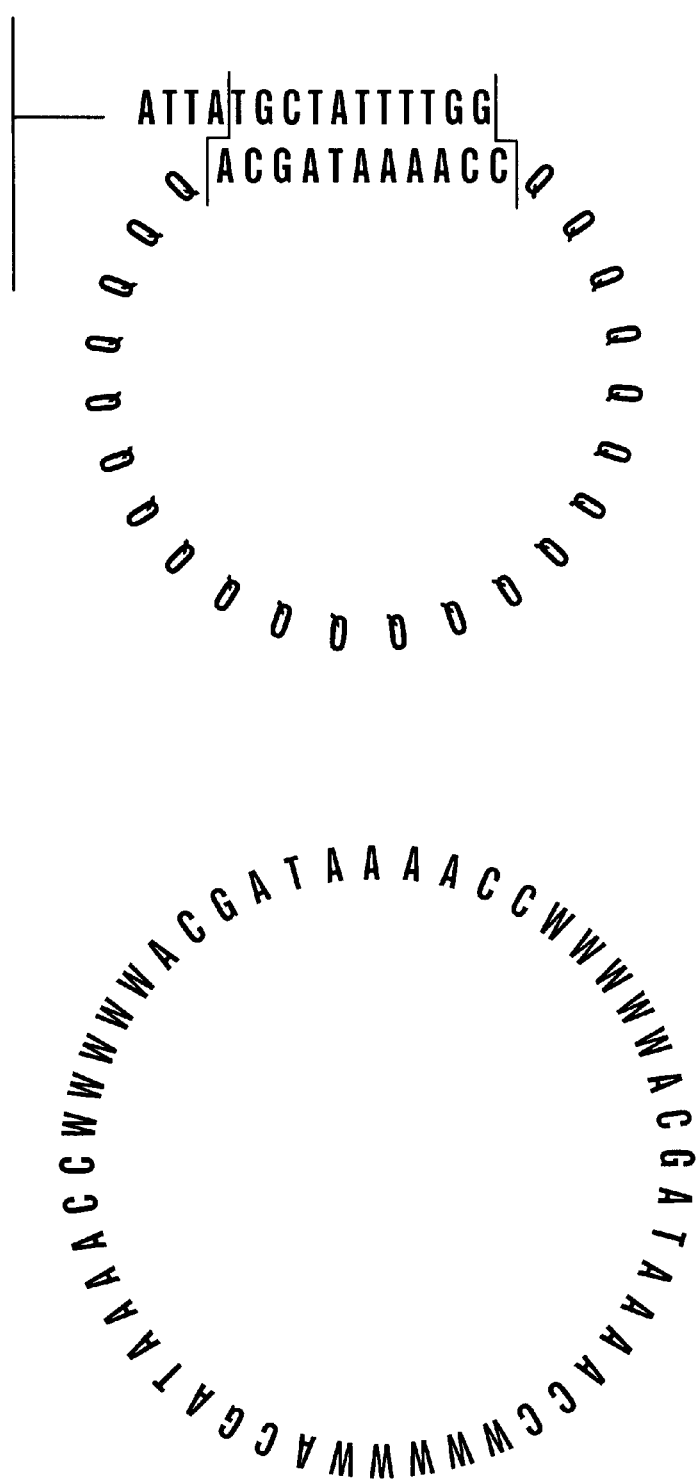
Figure 2:
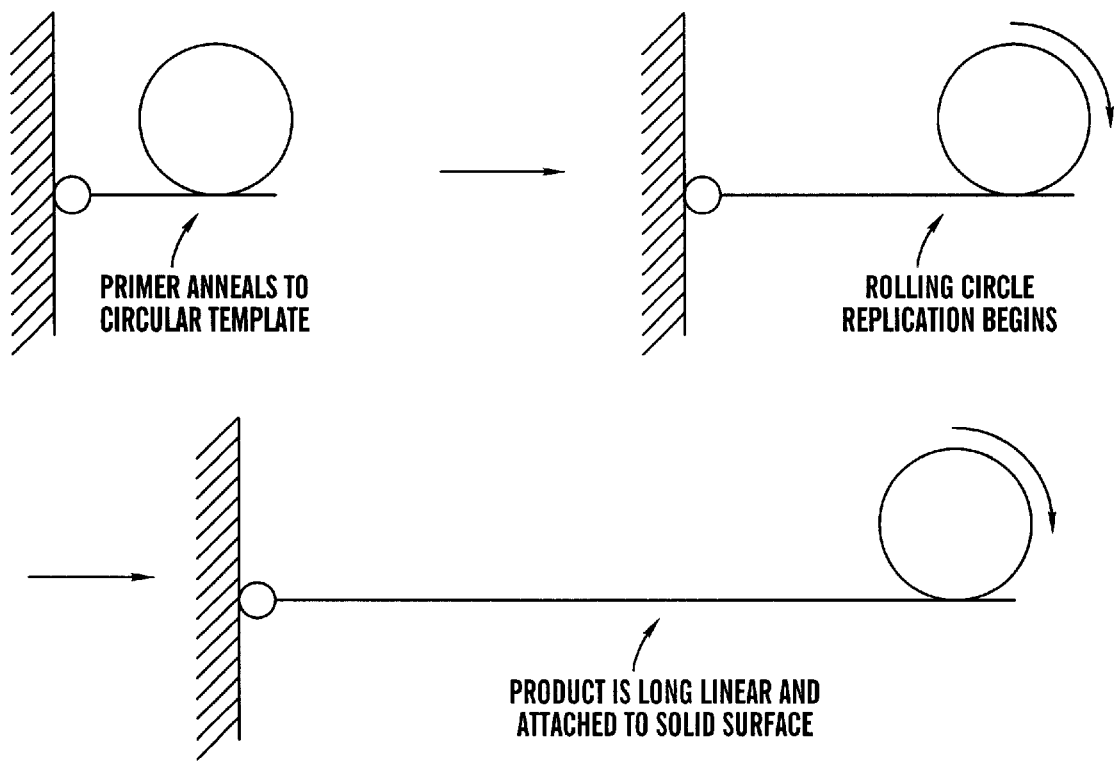
FIG. 2 is a schematic representation of Solid Surface Rolling Circle Amplification ("ssRCA"). The nucleic acid primer sequence is attached first to a surface and when a circular nucleic acid template is added, the primer hybridizes to the template. The template is then replicated by DNA polymerase (ie., the primer is extended).

Some of the reagents used in the practice of the present invention can be made using conventional techniques of molecular biology. Such techniques are described in the literature. For example, see *Molecular Cloning, A Laboratory, Manual*, 2nd Ed., ed. by Sambrook, Fritsch and Maniatis (Cold Spring Harbor Laboratory Press, 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986). In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); ng (nanograms); L (liters); ml (milliliters); μl (microliters); cm (centimeters); mm (millimeters); μm (micrometers); nm (nanometers); ° C. (degrees Centigrade); hr (hour); sec (second); min (minutes).

The present invention contemplates a method of generating an array, comprising providing a solid support comprising a plurality of positions for oligonucleotides, the positions defined by x and y coordinates; a plurality of identical oligonucleotides, each oligonucleotide comprising a sequence; and a plurality of unique circular DNA templates, each circular DNA template comprising a sequence of interest and a region complementary to at least a portion of the sequence of the oligonucleotides, the sequence of interest being different for each circular template; immobilizing one oligonucleotide from the plurality of identical oligonucleotides in each of the positions on the solid support to create an ordered array comprising a plurality of identical immobilized oligonucleotides; adding to each immobilized oligonucleotide of the ordered array a circular DNA template from the plurality of the unique circular DNA templates under conditions such that the immobilized oligonucleotide hybridizes to the circular DNA template to create a plurality of primed circular templates, each primed circular template comprising a different sequence of interest; and extending each of the primed circular templates to create an extended immobilized oligonucleotide comprising at least two copies of the sequence of interest, thereby generating an ordered redundant array.

In one embodiment of the present invention, oligonucleotides that are immobilized by the 5' end on a solid surface by a chemical linkage are contemplated. The oligonucleotides may approximately 17 bases in length, although other lengths are also contemplated.

In one embodiment of the present invention, the solid surface is selected from a group of materials comprising silicon, metal, and glass.

In another embodiment of the present invention, the immobilized oligonucleotides are attached to a complimentary nucleic acid stabilizer sequence.

In another embodiment of the present invention, the circular nucleic acid template is bacteriophage DNA, or non-bacteriophage DNA.

In another embodiment of the present invention, the extending step is achieved with a polymerase, wherein the polymerase is selected from a group comprising E. coli. DNA polymerase I, a fragment of E. coli. DNA polymerase I, or Φ29 DNA polymerase.

In another embodiment of the present invention, an ordered redundant array of immobilized oligonucleotides produced according to the above method is contemplated.

In another embodiment of the present invention, a method of hybridizing target nucleic acid fragments is contemplated providing the ordered redundant array of extended immobilized oligonucleotides of the above methods, a plurality of fragments of a target nucleic acid; and bringing the fragments of the target nucleic acid into contact with the array under conditions such that at least one of the fragments hybridizes to one of the extended immobilized oligonucleotides on the array.

In another embodiment of the present invention, a method of generating an array capable of hybridizing to fragments of a target nucleic acid is contemplated, comprising providing a solid support comprising positions for oligonucleotides, the positions defined by x and y coordinates; a plurality of oligonucleotides, each oligonucleotide comprising a sequence complementary to a different portion of the sequence of the target nucleic acid; and a plurality of corresponding circular DNA templates, each circular DNA template comprising a different portion of the sequence of the target; immobilizing each of the oligonucleotides in one of the positions on the solid support to create an ordered array comprising a plurality of immobilized oligonucleotides; adding to each immobilized oligonucleotide of the ordered array a corresponding circular DNA template under conditions such that the immobilized oligonucleotide hybridizes to the corresponding circular DNA template to create a plurality of primed circular templates; and extending the primed circular templates to create an ordered redundant array of extended immobilized oligonucleotides, each extended immobilized oligonucleotide comprising at least two copies of the portion of the sequence of the target nucleic acid.

In one embodiment of the present invention, oligonucleotides that are immobilized by the 5' end on a solid surface by a chemical linkage are contemplated. The oligonucleotides may approximately 17 bases in length, although other lengths are also contemplated.

In one embodiment of the present invention, the solid surface is selected from a group of materials comprising silicon, metal, and glass.

In another embodiment of the present invention, the immobilized oligonucleotides are attached to a complimentary nucleic acid stabilizer sequence.

In another embodiment of the present invention, the circular nucleic acid template is bacteriophage DNA, or non-bacteriophage DNA.

In another embodiment of the present invention, the extending step is achieved with a polymerase, wherein the polymerase is selected from a group comprising E. coli. DNA polymerase I, a fragment of E. coli. DNA polymerase I, or Φ29 DNA polymerase.

In another embodiment of the present invention, an ordered redundant array of immobilized oligonucleotides produced according to the above method is contemplated.

In another embodiment of the present invention, a method of hybridizing target nucleic acid fragments, is contemplated comprising the ordered redundant array of extended immobilized oligonucleotides of the above methods; a plurality of fragments of a target nucleic acid; and bringing the fragments of the target nucleic acid into contact with the array under conditions such that at least one of the fragments hybridizes to one of the extended immobilized oligonucleotides on the array.

However, it is not intended that the present invention be limited to specific examples of oligonucleotide primers or templates, specific reagents, or specific solid surfaces. A variety of oligonucleotide primers or templates, specific reagents, and specific solid surfaces are contemplated.

Importantly, it is not necessary to the successful use of the compositions, products, and methods of the present invention that one understand the precise mechanism by which the invention is achieved.

Experimental

The following examples serve to illustrate certain preferred embodiments and aspects of the present invention and are not to be construed as limiting the scope thereof.

EXAMPLE 1

Isolation of m13mp18 Circular DNA Templates

In this example, *Escherichia coli* bacteria were inoculated with m13mp18 bacteriophage (M13). The infected cells were grown overnight allowing the phage to multiply. Then the single stranded nucleic acid template sequences were harvested by centrifugation. As follows:

(a) Prepare LB Media.
(b) Grow *E. coli* TG1 on 1% LB-Agar plates for 1 day at 37° C.
(c) Prepare 2×TY Media.
(d) Grow an isolated colony of TG1 in 2×TY at 37° C. overnight.
(e) Transfer 500 ml of TG1 to 25 ml 2×TY and inoculate with 1 ml of M13mp18 stock. Grow for 5 hours at 37° C.
(f) Centrifuge at 15000 g for 15 min. Save supernatant.
(g) Add 1 g PEG 800 and 0.75 g NaCl. Stir for 40 mins.
(h) Centrifuge at 10000 g at 4° C. for 20 min.
(i) Add 1:8 ml Tris-HCl to dissolve and then collect in tubes.
(j) Add 150 ml phenol (pH 8). Vortex 30 sec. Let stand 1 min. Repeat. Centrifuge at 12000 g at 4° C. for 2 min. Remove top layer to new tube.
(k) Add 150 ml chloroform. Vortex briefly. Let stand. Centrifuge at 12000 g at 4° C.
(l) Transfer upper phase to new tubes that contain 900 ml 25:1 EtOH:3 M Sodium.
(m) Recover precipitate by centrifuging at 12000 g at 4° C. for 10 min.
(n) Gently aspirate and recentrifuge (~15 sec) to remove residual supernate.
(o) Add 200 ml 70% EtOH. Vortex briefly. Centrifuge and immediately remove supernatant as above.
(p) Use speedvac to dry pellet of residual EtOH.
(q) Dissolve in 20 ml TE (pH 8.0).
(r) Repeat from step (j).
(s) Store at −20° C.

The single stranded template sequences that are harvested can be used as nucleic acid template sequences according to the method of the present invention.

EXAMPLE 2

Creation of Long Primers For ssRCA

This example involves two small PCR primers that were selected and used to make a longer primer suitable for ssRCA. The primers are selected so that the 5' end of the long primer could be biotinylated and that 3' end will have ~20 bases that are complementary to M13. This example involved the creation of the 226 base RCA primer known as C9. C9 is a hybrid primer that was constructed by performing PCR on a M13 derivative called MGP1-2. The 5'region of C9 is mostly native T7 polymerase DNA and the 3 prime region is M13 DNA.

(a) Two primers were selected using computer program PRIME from GCG computer package.
   (i) P1: 5'-CAA TTT CAC ACA GGC CCA AG (SEQ ID NO: 10)
   (ii) P2: 5'-XCG TAA GAC TCA TGC TCA AGC X=Biotin (SEQ ID NO: 11)
(b) PCR Reaction Mixture:

|  | dNTP (2.5 mM) | Primer 1 [10 mM] | Primer 2 [10 mM] | MGP 1–2 1:70 | MgCl$_2$ [25 mM] | 10X PCR Buffer | AmpliTaq 1:8 | Total Volume |
|---|---|---|---|---|---|---|---|---|
| Final Concl. | 375 mM | 1 mM | 1 mM | 0.6 ng/ml | 2.5 mM | 1.25 X | 5 U | 20 ml |

(c) Thermal Controller Program:

| Step | Time | Temp |
|---|---|---|
| 1 | 1 min. | 90° C. |
| 2 | 1 min. | 56° C. |
| 3 | 1 min. | 65° C. |
| 4 | 30 sec | 90° C. |
| 5 | 25 times to step 2 | |
| 6 | 7 min | 72° C. |
| 7 | 99 hr. | 4° C. |
| 8 | END | |

The long primer sequences can be used as nucleic acid primer sequences according to the method of the present invention.

EXAMPLE 3

Creation of Short Primers For ssRCA

In similar reaction conditions as in Example 2, a shorter 17 base DNA primer was also made. It was biotinylated on the 5' end and was entirely complimentary to m13mp18 DNA. A 17 base long primer was used in a solid surface RCA reaction run in a 1% agarose gel (results not shown). In these experiments, one lane was loaded with single stranded circular M13 DNA which was used as a standard of 7.25 kb, while other lanes were represented ssRCA reactions, and still other lanes contained positive and negative controls (ie., there were multiple positive control and multiple negative control lanes used in this experiment). For the lanes containing the ssRCA reactions, smearing and collection of DNA in the wells was observed, as was the case of in the positive control lanes. The negative control lanes generally showed no collection of DNA in the wells. However, in two lanes containing negative controls, collection of DNA was observed. The smearing is indicative of an RCA reaction, where product sizes vary. Also, the collection of DNA in the wells indicates a high molecular weight product (>20 kb). The DNA collection in the wells of two lanes loaded with negative control material was much smaller than that seen in the other RCA and ssRCA lanes. In addition, the Reaction yield was higher with the shorter primer. The short primer sequences of this example can be used as nucleic acid primer sequences according to the method of the present invention.

EXAMPLE 4

Attachment of Single Stranded Primers To M-280 Stv Coated Magnetic Beads

In this example, a protocol is demonstrated to purify a biotinylated nucleic acid primer sequence from the complementary nonbiotinylated nucleic acid sequence, and attach the biotinylated nucleic acid sequence primer to the M-280 Stv coated magnetic beads (Dynal Inc.). As follows:

(a) Wash 1.5 mg M-280 Stv coated magnetic beads (Dynal Inc.) three times in TE(pH 8.0) on magnetic separator. Resuspend beads in 30 ml TE (pH 8.0). Store at 4° C.
(b) Bring 100 pmoles of primer to final concentration of 0.01 M NaOH.
(c) Boil primer mix for 10 minutes in water bath.
(d) Immediately cool on ice for 2 min.
(e) To bead mixture of step (a), add primer mix.
(f) Let stand for 20 seconds on magnetic separator. Then remove supernatant.
(g) Wash twice with TE (pH 8.0). Resuspend in 30 ml TE. (pH 8.0).
(h) Store at 4° C.

This example represents the immobilization of a nucleic acid primer sequence to a solid surface.

EXAMPLE 5 ssRCA Reaction

This is an example of the protocol for the ssRCA reaction. In this reaction, the single stranded DNA primer that was attached to the bead in Example 4 is extended via ssRCA into a long linear DNA molecule that is a concatamer of M13 DNA. This product remains attached to the bead.

(a) ssRCA Reaction Mixture

|  | dNTP [2.5 mM] | Primer | M13 1:4 | 10X PCR Buffer | DNA Pol I @ Step 2 | Total Volume |
|---|---|---|---|---|---|---|
| Final Concl. | .225 mM | 1 mM | 200 ng/ml | 1 X | 10 U | 100 ml |

(b) Thermal Controller Program

| Step | Time/Temp. |
|---|---|
| 1 | 3 min./60° C. |
| 2 | 3 min./60° C. |
| 3 | 7 hr./37° C. |

-continued

| Step | Time/Temp. |
| --- | --- |
| 4 | 99 hr./4° C. |
| 5 | END |

EXAMPLE 6

Template Circularization and RCA in Solution

Figure 3A:
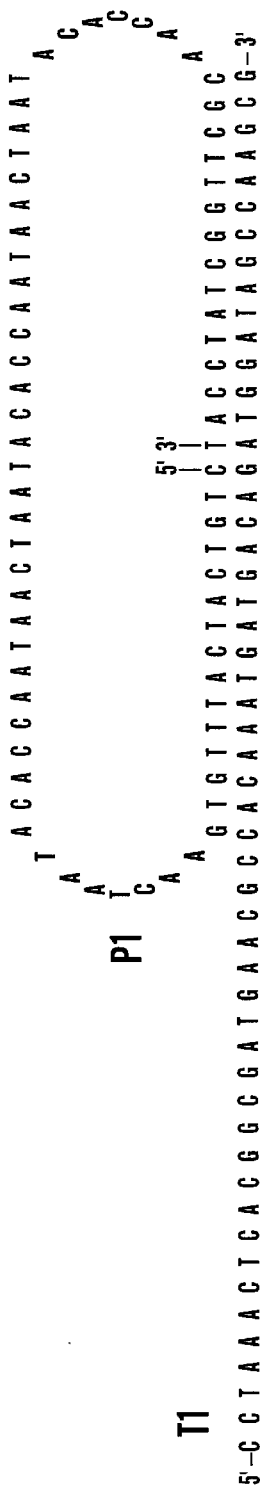
FIG. 3A is a diagram of Oligonucleotide sequences used in RCA. The 74-base template nucleic acid sequences, P1 (SEQ ID NO: 4) and P2 (SEQ ID NO: 7) were purchased with a 5'-phosphate, PAGE purified from Bio-Synthesis, Inc. The 53-base primer nucleic acid sequences, T1 (SEQ ID NO: 5) and T2 (SEQ ID NO: 6) were purchased with a 5'-biotin modification, HPLC purified from Operon Technologies. The 5'–15 bases, and 3'–15 bases of P1 are complementary to positions 23–38, and 39–44 of T1, respectively. The P1/T2 complex contained a C:T mismatch at the 5'-terminus of P1; the P2/T2 complex is similar in sequence to P1/T2, except that the C:T mismatch occurs at the 3'-terminus of P2. The single stranded nucleic acid sequence, A12 (SEQ ID NO: 8) (Operon Technologies), is complementary to the 5'-end of T1 and T2, and is used for structural support in chip-based experiments.
Figure 3A:
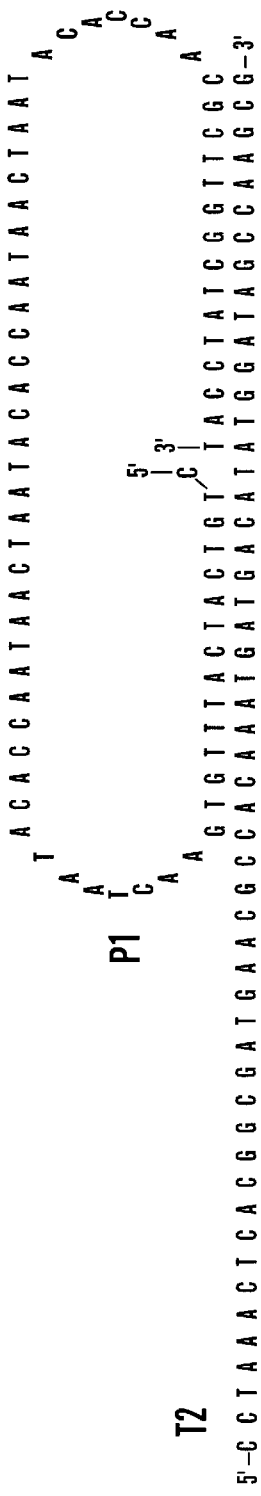
Figure 3A:
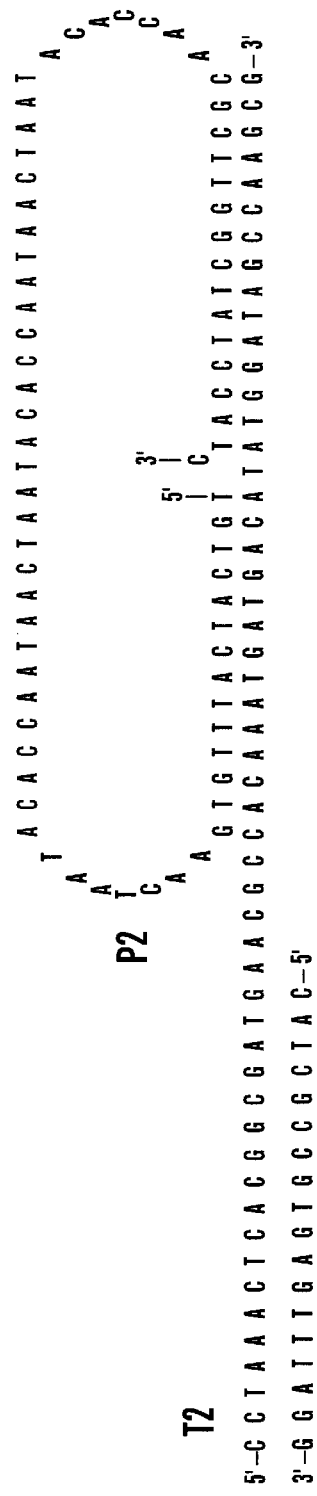
Figure 3B:
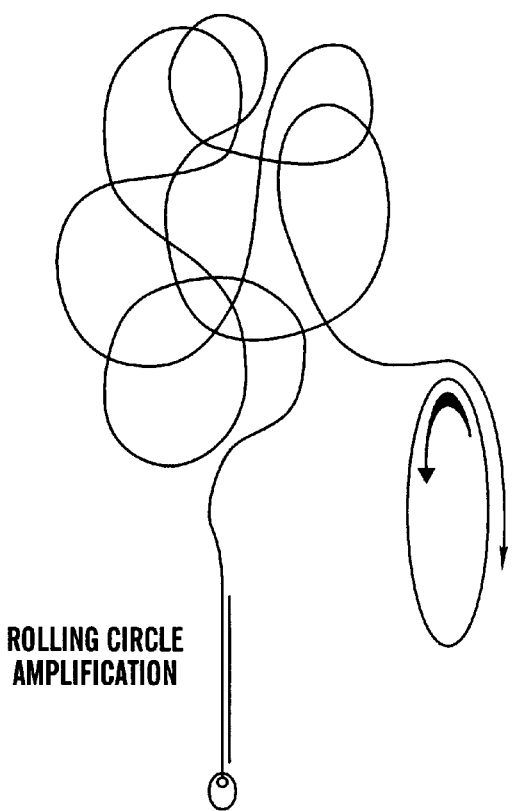
FIGS. 3B and 3C depict the effect of polymerization using a circular (ligated) template sequence as compared to polymerization on an uncircularized (non-ligated) template sequence.
Figure 3C:
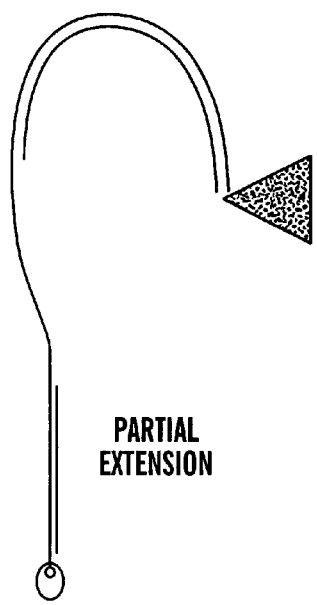

The sequences and base paring of a P1/T1 complex are shown in FIG. 3A. P1 (SEQ ID NO: 4) circularization was performed in solution by combining equimolar ratios of P1 and T1 (SEQ ID NO: 5) to a final concentration of 5 mM in TE (10 mM Tris-Cl, 1 mM EDTA) supplemented with 0.1M NaCl, heating the mixture to 95° C., followed by slowly cooling to room temperature. Ten pmol of the P1/T1 complex and 400 U T4 DNA ligase (New England Biolabs) were suspended in 50 ml of T4 DNA ligase buffer supplied by the manufacturer. The cocktail was incubated at 16° C. for 30 min in a PCR thermocycler, and the reaction was terminated by heating the samples to 75° C. for 15 min. Non-ligated controls were made by omitting ligase from the above reaction.

Figure 4A:
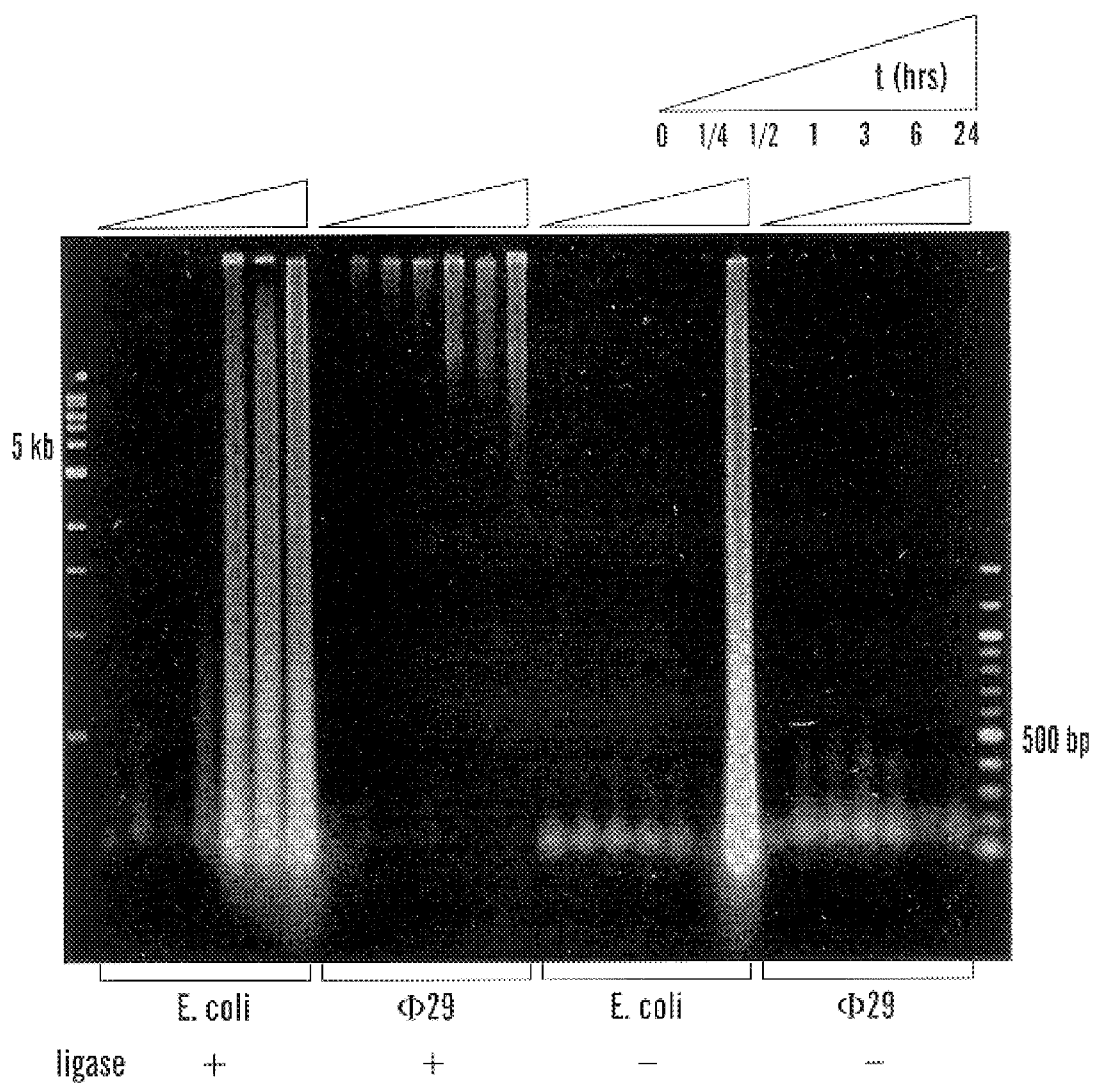
FIG. 4A represents the kinetics of RCA produced by Φ29 or *E. coli* DNA polymerases. RCA amplifications were resolved on a 0.8% agarose gel, and stained with SYBRII, which is a DNA intercalating dye which can stain both double-stranded and single-stranded DNAs, but shows enhanced fluorescence when bound to duplexes. The incubation times were 0, ¼, ½, 1, 3, 6 and 24 hr, respectively. One kb and 100 bp makers were loaded in the first and last lanes, respectively. RCA was performed using ligated (+) or non-ligated (–) P1 nucleic acid template sequences as indicated at the bottom of the image, and T1 nucleic acid primer sequences.
Figure 4B:
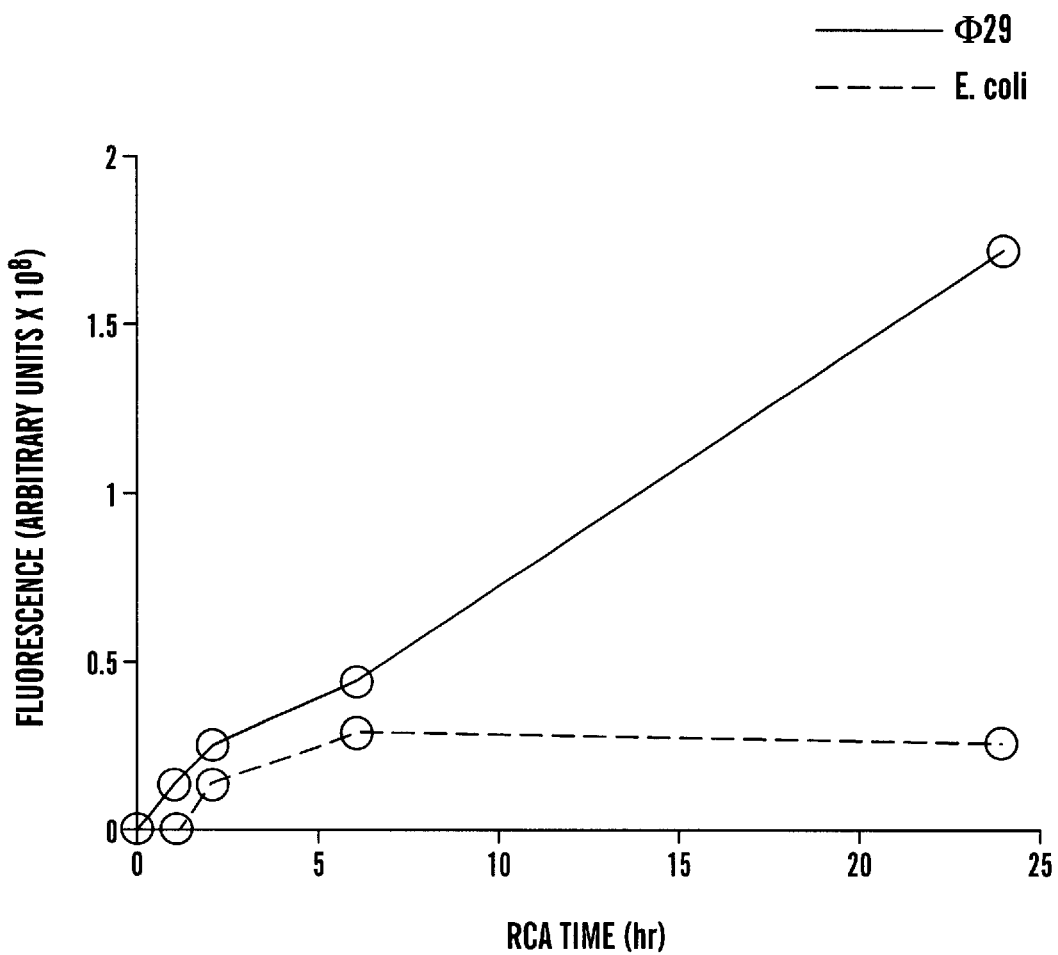
FIG. 4B represents the fluorescence intensity measurement of RCA concatamers that was determined by scanning the concatamers with a Molecular Dynamics STORM imager. The x-axis represents RCA incubation times, and the y-axis is florescence. The readings were taken by the hybridization of 5'-fluorescein-labeled (F) oligonucleotide (5'-FAACTAATACACCAA (SEQ ID NO: 9)) to RCA concatamers immobilized on nitrocellulose membranes by UV crosslinking. Hybridization was carried out overnight at 25° C. in 6×SSC buffer, followed by a 15 min wash in 6×SSC, and a 15 min wash in 2×SSC.

Both circular and linear P1 templates were used as templates for RCA. P1 template sequences were circularized on T1 primer sequences using T4 DNA ligase. Ligation products were analyzed on 12% denaturing polyacrylamide gels; circularized P1 sequence product was observed as a supershifted band from the linear form. Approximately 60% of the P1 templates were circularized when equimolar ratios of P1 and T1 were ligated for 30 min at 16. Aliquots of either linear or circular P1 were used as templates for RCA reactions. The kinetics of RCA was explored by different incubation times of the P1/T1 complexes with E. coli DNA polymerase I or Φ29 DNA polymerase. FIG. 4A shows the resulting amplification resolved on a 0.8% agarose gel. The gel was stained with SYBRII (FMC), a single-strand specific nucleic acid dye. The RCA amplification generated from DNA polymerase I and Φ29 DNA polymerase showed remarkable differences. Note that circularized P1 sequence RCA products increase over time, for incubation periods up to 24 hr. DNA polymerase I also generated amplifications with linear P1/T1 complexes after long incubation periods (between 6 and 24 hr), but not nearly at the same rate as the Φ29 DNA polymerase; see FIG. 4B.

EXAMPLE 7

Fabrication of Streptavidin-Coated Microwells

Microwells were etched in silicon. A 3" diameter silicon wafer contained approximately 250 microwells, with dimensions 2 mm×2 mm×200 mm deep, and spaced 2 mm apart. Biotin was discretely patterned inside the microwells using photolithography that is well known in the art. Briefly, the micromachined wafers were silanized and an ethanolic solution of photoactivatable biotin (Pierce) was deposited on the wafers and allowed to evaporate. Photoactivatable biotin forms covalent bonds with nearby organic moieties upon exposure to UV light. A photomask was placed over the wafer such that only the microwells were exposed to UV light. The irradiated wafer was washed and then incubated with streptavidin, which only binds inside the biotinylated microwells. Because of streptavidin's tetrameric structure, two biotin-binding sites are used to immobilize the protein, leaving the remaining sites available to bind biotinylated oligonucleotides. Each well has a 500 nl volume.

EXAMPLE 8

Target Immobilization and RCA Performed on Silicon Chips

This example involves the 18-base oligonucleotide, A12, which is complementary to the first 5'–18 bases of T1 and T2, and serves as a structural support (i.e., stabilizer) to lift the nucleic acid strands from the surface. Equimolar ratios of T1/A12 and T2/A12 were suspended at a final concentration of 5 mM in TE supplemented with 0.1M NaCl, heated to 95° C., followed by slowly cooling to room temperature. Five hundred nl (1250 fmol) of both DNA complexes were spotted inside streptavidin-coated microwells. The chip was saturated with 50 mM biotin in SPE buffer (0.1M Na-phosphate, pH 6.6, 1M NaCl), then washed 4×15 min in SPE buffer at 37° C., rinsed briefly with deionized $H_2O$, and air dried. A hybridization slide chamber (CoverWell PC50, Grace Bio-labs) was placed over the chip and secured with small paper binding clips. Two small holes were punctured in the hybridization chamber and served as fluid inlet and outlet ports. Hybridization was performed by injecting 85 ml of the indicated template solution suspended in TE supplemented with 0.1M NaCl. The injection ports were sealed, and the chip was incubated for 12 hr at 37° C. The chip was washed 4×15 min in SPE buffer at 37° C., followed by a rinse in deionized $H_2O$. A new hybridization chamber was placed on the chip and 85 ml of ligation cocktail was injected onto the chip and incubated for 30 min. The chip was washed 4×15 min in SPE buffer at 37° C., rinsed in deionized $H_2O$, and DNA polymerase cocktail was added. The chip was washed 4×15 min in SPE buffer before exposing to phosphorimaging plates. A Molecular Dynamics STORM imager was used to scan the plates, and analysis was performed using software provided by the manufacturer. Thus, this example represents the immobilization of a nucleic acid primer sequence to a solid surface, and further amplification of the nucleic acid sequences on that surface.

EXAMPLE 9

Single Nucleotide Polymorphism Detection on Silicon Chips

Figure 5A:
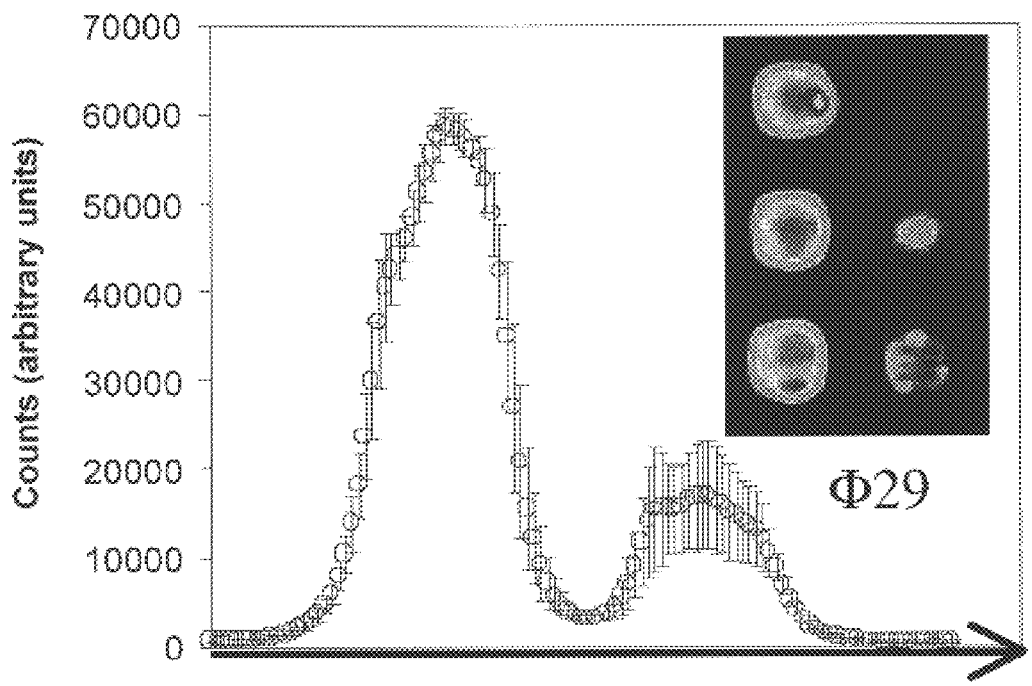
FIG. 5 depicts autoradiograms that show a solid surface format using a patterned streptavidin microwell chip. Each chip comprised of six microwells. Two target oligonucleotide sequences differing by a single base substitution were spotted in triplicate in the microwells. The following assays were performed in parallel on the immobilized target sequences. Assay volumes were 25 ml. A hybridization chamber was placed over the chip to contain the solutions. First, the chip was incubated with templates overnight, followed by a wash. Then, ligation was performed for 30 min, followed by a wash. Lastly, DNA polymerase and nucleotides, including [a-$^{32}$P]-dTTP were added and incubated for 6 hours.
Figure 5B:
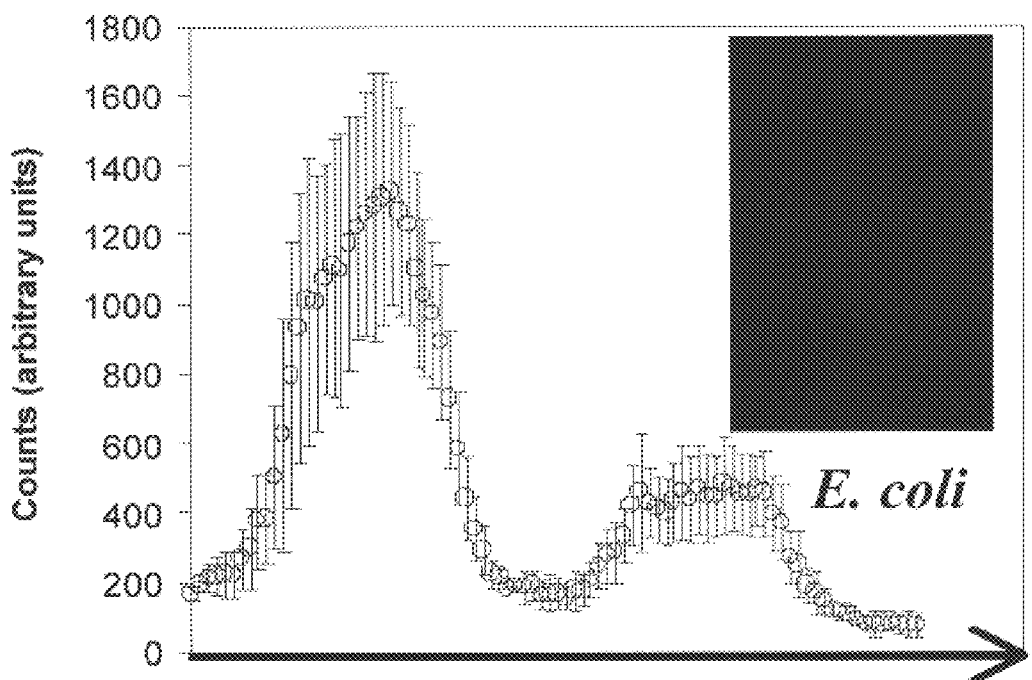

In this example, it is shown that the ability of Φ29 to generate significant amounts of RCA product using circularized templates is equally applicable to amplify surface-bound primer nucleic acid sequences. Two biotinylated primer nucleic acid sequences, T1 and T2, differing only at position 38, were immobilized inside streptavidin-coated microwells. The 5'-terminus of the P1 template aligns with target positions 38, forming a C:G basepair and a C:T mismatch with T1 and T2, respectively. The P2/T2 complex contained a C:T mismatch at the 3'-terminus of P2 and position 38 of T2. Chip-based SNP detection was performed in three steps. The chips were incubated overnight with the templates in a solution of TE supplemented with 0.1M NaCl, and washed 4×15 min with SPE buffer to remove non-hybridized templates. Ligation was performed with T4 DNA ligase for 30 min at 37° C. followed by a wash. Chips were then incubated with DNA polymerase in the presence of dNTPs and [a-32P] dTTP for 12 hr at 31° C. The chip was washed to remove unincorporated nucleotides, before radio-active imaging. Line profiles were determined using ImageQuant software (Molecular Dynamics). In general, even the mismatched template/target complexes gave significant signals, and optimal conditions for SNP discrimination were determined by using different polymerases, varying the template concentrations, and adjusting the ligation conditions. FIGS. 5A and 5B show autoradiograms of the chips with line profiles above the images. The specific reaction conditions are given in the Figures.

As shown in the Figure, Φ29 DNA polymerase was more stringent and efficient in amplifying closed switches (i.e., circularized templates) than *E. coli* DNA polymerase I.

The ligation conditions which produced the best discrimination between matched and mismatched templates consisted of 4U/ml T4 DNA ligase, 1M NaCl, and incubation at 37° C. for 30 min. Under our most stringent conditions, the two primer sequences could be distinguished with a signal-to-noise ratio of ~103.

EXAMPLE 10

Increased Volume Density of Nucleic Acid Sequences

Figure 6:
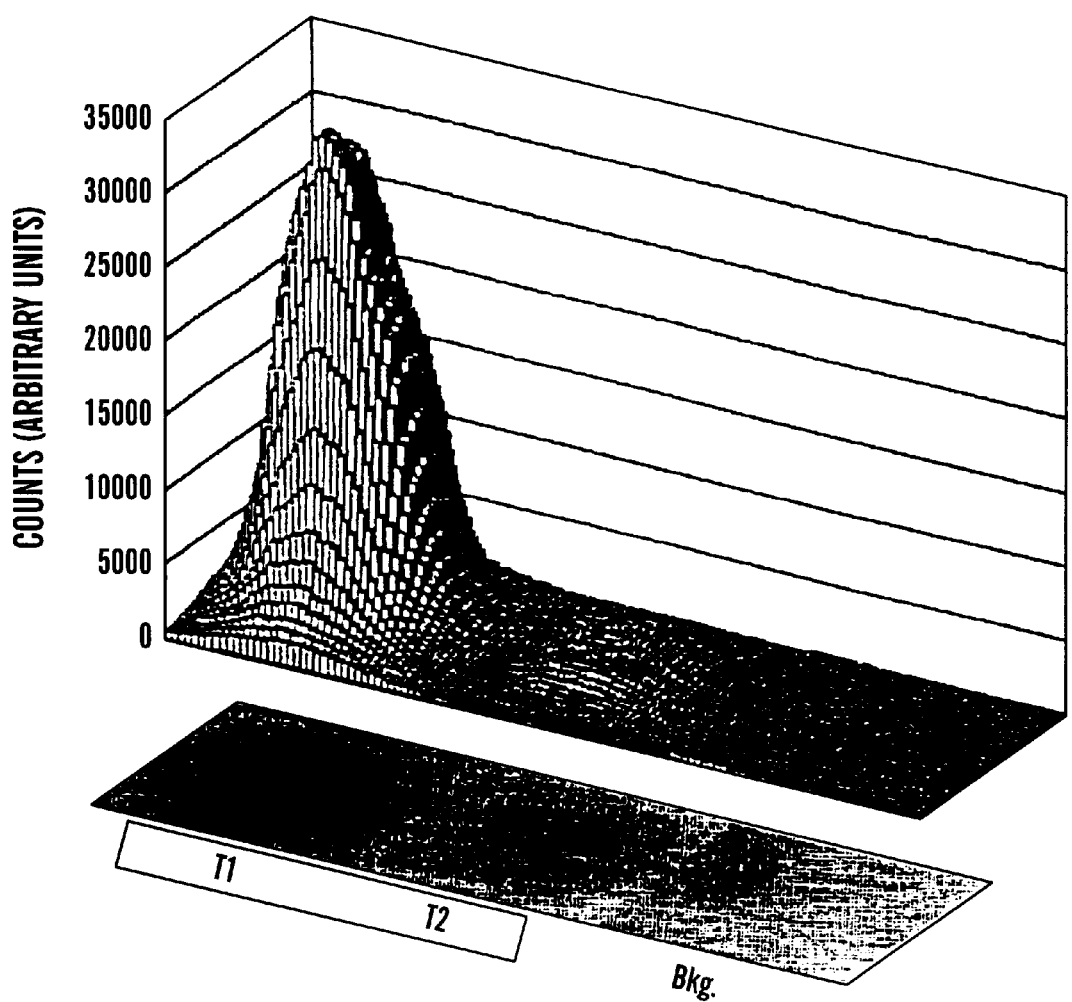
FIG. 6 illustrates a phosphorimager scan of three wells of enzymatically-enhanced DNA arrays after primer extension with Φ29 DNA polymerase in the presence of [α-32$_P$] dTTP. Primer T1 and T2 were immobilized in the left and middle wells, respectively, and the right well (Bkg) was left blank for a background reference. P2 was used as the template for hybridization and circularization. The plot above the image shows the counts for each pixel in the scan. Total radioactive counts for T1, T2 and the background were 3,180,000, 255,000 and 43,000, respectively. This indicates that the discrimination of single-based polymorphisms was increased at a 12 fold rate from T1 over T2, which in turn increases the volume density of the nucleic acid sequences.

As demonstrated by FIG. 6, a phosphorimager scan of three wells of enzymatically-enhanced DNA arrays after primer extension with Φ29 DNA polymerase in the presence of [α-32P] dTTP. Primers T1 and T2 were immobilized in the left and middle wells, respectively, and the right well (Bkg) was left blank for a background reference. P2 was used as the template for hybridization and circularization. Φ29 DNA polymerase was used to amplify the primer T1 well, and DNA polymerase I was used to amplify the primer T2 well. The plot above the image shows the counts for each pixel in the scan. Total radioactive counts for T1, T2 and the background were 3,180,000, 255,000 and 43,000, respectively. This indicates that the discrimination of single-based polymorphisms was increased at a 12 fold rate from T1 over T2, which in turn indicates an increased volume density of the nucleic acid sequences. Notice that the reaction yield (hence, volume density) was higher with the Φ29 DNA polymerase that was used.

Based on the above disclosure, embodiments, and experiments, those skilled in the art will recognize, or be able to ascertain using no more than routine experimentation, many equivalents to the specific embodiments of the invention described herein. Such equivalents are intended to be encompassed by the following claims.

We claim:

1. A method of generating an array, comprising:
   (a) providing: i) a solid support comprising a plurality of positions for oligonucleotides, said positions defined by x, and y coordinates; ii) a plurality of identical oligonucleotides, each oligonucleotide comprising a sequence; and iii) a plurality of unique circular DNA templates, each circular DNA template comprising a sequence of interest and a region complementary to at least a portion of said sequence of said oligonucleotides, said sequence of interest being different for each circular template;
   (b) immobilizing one oligonucleotide from said plurality of identical oligonucleotides in each of said positions on said solid support to create an ordered array comprising a plurality of identical immobilized oligonucleotides;
   (c) adding to each immobilized oligonucleotide of said ordered array a circular DNA template from said plurality of said unique circular DNA templates under conditions such that said immobilized oligonucleotide hybridizes to said circular DNA template to create a plurality of primed circular templates, each primed circular template comprising a different sequence of interest; and
   (d) extending each of said primed circular templates along a z coordinate to create an extended immobilized oligonucleotide comprising at least two copies of said sequence of interest, thereby generating an ordered redundant array, wherein said ordered redundant array refers to said array having at least two copies of said sequence of interest along the z coordinate.

2. The method of claim 1, wherein said oligonucleotides are immobilized on a solid surface by a chemical linkage.

3. The method of claim 1, wherein said oligonucleotides are immobilized on said solid surface by the 5' end of said oligonucleotides.

4. The method of claim 1, wherein said oligonucleotides are approximately 17 bases in length.

5. The method of claim 1 wherein said solid surface is selected from a group of materials comprising silicon, metal, and glass.

6. The method of claim 1 wherein said immobilized oligonucleotides are attached to a complimentary nucleic acid stabilizer sequence.

7. The method of claim 1, wherein said circular nucleic acid template is bacteriophage DNA.

8. The method of claim 1, wherein said circular nucleic acid template is non-bacteriophage DNA.

9. The method of claim 1, wherein said extending in step (d) is achieved with a polymerase.

10. The method of claim 9, wherein said polymerase is selected from a group comprising E. coli DNA polymerase I, a fragment of E. coli. DNA polymerase I, or Φ29 DNA polymerase.

11. A method of hybridizing target nucleic acid fragments, comprising:
   (a) providing i) an ordered redundant array of immobilized oligonucleotides produced according to the method of claim 1, wherein said array comprises a plurality of identical immobilized oligonucleotides, wherein each immobilized oligonucleotide has a circular DNA containing a sequence of interest that has been extended along the z coordinate to have at least two copies of said sequence of interest; and ii) a plurality of fragments of a target nucleic acid; and
   (b) bringing said fragments of said target nucleic acid into contact with said array under conditions such that at least one of said fragments hybridizes to one of said extended immobilized oligonucleotides on said array.

12. A method of generating an array capable of hybridizing to fragments of a target nucleic acid, comprising:
   a) providing: i) a solid support comprising positions for oligonucleotides, said positions defined by x and y coordinates; ii) a plurality of oligonucleotides, each oligonucleotide comprising a sequence complementary to a different portion of the sequence of said target nucleic acid; and iii) a plurality of corresponding circular DNA templates, each circular DNA template comprising a different portion of the sequence of said target;
   b) immobilizing each of said oligonucleotides in one of said positions on said solid support to create an ordered array comprising a plurality of immobilized oligonucleotides;
   c) adding to each immobilized oligonucleotide of said ordered array along a z coordinate a corresponding circular DNA template under conditions such that said immobilized oligonucleotide hybridizes to said corresponding circular DNA template to create a plurality of primed circular templates; and
   d) extending said primed circular templates to create an ordered redundant array of extended immobilized oligonucleotides, each extended immobilized oligonucleotide comprising at least two copies of said portion of said sequence of said target nucleic acid, wherein said ordered redundant array refers to said array having at least two copies along the z coordinate of said portion of the sequence of interest contained in said primed circular template.

13. The method of claim 12, wherein said oligonucleotides are immobilized on a solid surface by a chemical linkage.

14. The method of claim 12, wherein said oligonucleotides are immobilized on said solid surface by the 5' end of said oligonucleotides.

15. The method of claim 12, wherein said oligonucleotides are approximately 17 bases in length.

16. The method of claim 12 wherein said solid surface is selected from a group of materials comprising silicon, metal, and glass.

17. The method of claim 12 wherein said immobilized oligonucleotides are attached to a complementary nucleic acid stabilizer sequence.

18. The method of claim 12, wherein said circular nucleic acid template is bacteriophage DNA.

19. The method of claim 12, wherein said circular nucleic acid template is non-bacteriophage DNA.

20. The method of claim 12, wherein said extending in step (d) is achieved with a polymerase.

21. The method of claim 20, wherein said polymerase is selected from a group comprising *E. coli*. DNA polymerase I, a fragment of *E. coli*. DNA polymerase I, or Φ29 DNA polymerase.

22. A method of hybridizing target nucleic acid fragments, comprising:

a) providing i) an array capable of hybridizing to fragments of a target nucleic acid produced according to the method of claim 12; and ii) a plurality of fragments of a target nucleic acid; and b) bringing said fragments of said target nucleic acid into contact with said array under conditions such that at least one of said fragments hybridizes to one of said extended immobilized oligonucleotides on said array.

* * * * *

SEQUENCE LISTING

<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: recombinant

<400> SEQUENCE: 1
attatgctat tttgg                                                    15

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: recombinant

<400> SEQUENCE: 2 aaaacc                                                               6

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: recombinant

<400> SEQUENCE: 3
acgataaaac c                                                        11

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence: recombinant

<400> SEQUENCE: 4
ctgtcatcat ttgtgaacta atacaccaat aactaataca ccaataacta atacaccaac    60
gcttggctat ccat    74

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: recombinant

<400> SEQUENCE: 5
cctaaactca cggcgatgaa cgccacaaat gatgacagat ggatagccaa gcg    53

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: recombinant

<400> SEQUENCE: 6
cctaaactca cggcgatgaa cgccacaaat gatgacatat ggatagccaa gcg    53

<210> SEQ ID NO 7
<211> LENGTH: 74
<212> TYPE: DNA
<213> ORGANISM: Artificial Sequence
<220> FEATURE:
<223> OTHER INFORMATION: Description of Artificial Sequence: recombinant

<400> SEQUENCE: 7
tgtcatcatt tgtgaactaa taccaata actaatacac caataactaa taccaacg    60
cttggctatc catc    74

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: recombinant

<400> SEQUENCE: 8
catcgccgtg agtttagg    18

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: recombinant

<400> SEQUENCE: 9
aactaataca ccaa    14

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: recombinant

<400> SEQUENCE: 10
caatttcaca caggcccaag    20

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: recombinant

<400> SEQUENCE: 11
cgtaagactc atgctcaagc                                                    20
```